(12) United States Patent
Qiu et al.

(10) Patent No.: US 12,343,062 B2
(45) Date of Patent: Jul. 1, 2025

(54) METHOD AND DEVICE FOR CONTROLLING OUTPUT OF RADIOFREQUENCY ABLATION POWER, AND RADIOFREQUENCY ABLATION SYSTEM

(71) Applicant: HANGZHOU NUO CHENG MEDICAL INSTRUMENT CO., LTD., Zhejiang (CN)

(72) Inventors: Xinjiong Qiu, Zhejiang (CN); Xiongzhi Wang, Zhejiang (CN); Daoyang Liu, Zhejiang (CN); Shanfeng Hu, Zhejiang (CN); Bobo Peng, Zhejiang (CN); Tingchao Zhang, Zhejiang (CN); Liwen Liu, Zhejiang (CN)

(73) Assignee: HANGZHOU NUO CHENG MEDICAL INSTRUMENT CO., LTD., Hangzhou (CN)

( * ) Notice: Subject to any disclaimer, the term of this patent is extended or adjusted under 35 U.S.C. 154(b) by 569 days.

(21) Appl. No.: 17/848,222

(22) Filed: Jun. 23, 2022

(65) Prior Publication Data
US 2022/0313346 A1 Oct. 6, 2022

Related U.S. Application Data

(63) Continuation of application No. PCT/CN2020/130823, filed on Nov. 23, 2020.

(30) Foreign Application Priority Data

Dec. 24, 2019 (CN) .......................... 201911351693.8

(51) Int. Cl.
*A61B 18/12* (2006.01)
*A61B 18/14* (2006.01)
*A61B 18/00* (2006.01)

(52) U.S. Cl.
CPC .......... *A61B 18/1206* (2013.01); *A61B 18/14* (2013.01); *A61B 2018/00577* (2013.01);
(Continued)

(58) Field of Classification Search
CPC ..... A61B 18/12; A61B 18/1206; A61B 18/14; A61B 2018/00577; A61B 2018/00642;
(Continued)

(56) References Cited

U.S. PATENT DOCUMENTS

| 5,871,481 A * | 2/1999 | Kannenberg | ....... A61B 18/1206 606/41 |
| 6,409,722 B1 * | 6/2002 | Hoey | ..................... A61B 18/18 606/41 |

(Continued)

*Primary Examiner* — Michael F Peffley
(74) *Attorney, Agent, or Firm* — LEASON ELLIS LLP

(57) ABSTRACT

A method and apparatus for controlling output of radio frequency ablation power, and a radio frequency ablation system. The method for controlling output of radio frequency ablation power comprises: when a starting signal is received, controlling a radio frequency energy generator to output a preset ablation power, recording ablation time, and acquiring an actual ablation parameter (102), wherein the actual ablation parameter comprises the actual impedance; when the actual impedance meets any one of a first preset condition and a second preset condition, controlling the radio frequency energy generator to suspend output of the ablation power, recording sleep time, and suspending recording of the ablation time (105); and if the sleep time exceeds a sleep time threshold value, controlling the radio frequency energy generator again to continue to output the ablation power, and continuing to record the ablation time (107), wherein the first preset condition is: $R > K_1 \times Rmin_1$, and the second preset condition is: $R > K_2 \times Rmin_2$. According to the method, the impedance of an ablation part is enabled to be in an intermittent stably-changing state, and continuous output of radio frequency energy can be ensured, such (Continued)

that radio frequency ablation is relatively uniformly performed in a cyclic manner.

20 Claims, 5 Drawing Sheets

(52) U.S. Cl.
CPC ........... *A61B 2018/00642* (2013.01); *A61B 2018/00678* (2013.01); *A61B 2018/00702* (2013.01); *A61B 2018/00791* (2013.01); *A61B 2018/00875* (2013.01); *A61B 2018/00886* (2013.01)

(58) Field of Classification Search
CPC ........... A61B 2018/00678; A61B 2018/00702; A61B 2018/00791; A61B 2018/00875; A61B 2018/00886
USPC .......................................................... 606/34
See application file for complete search history.

(56) References Cited

U.S. PATENT DOCUMENTS

| | | | |
|---|---|---|---|
| 8,211,100 B2* | 7/2012 | Podhajsky | A61B 18/1206 |
| | | | 606/34 |
| 9,717,552 B2* | 8/2017 | Cosman | A61B 18/14 |
| 2013/0035679 A1* | 2/2013 | Orszulak | A61B 18/1445 |
| | | | 330/69 |
| 2023/0320781 A1* | 10/2023 | Liu | A61B 18/1492 |
| | | | 606/41 |

* cited by examiner

METHOD AND DEVICE FOR CONTROLLING OUTPUT OF RADIOFREQUENCY ABLATION POWER, AND RADIOFREQUENCY ABLATION SYSTEM

CROSS-REFERENCE TO RELATED APPLICATIONS

This application is a continuation of International Application No. PCT/CN2020/130823 filed on Nov. 23, 2020, which claims the priority of Chinese Patent Application No. 201911351693.8 filed to the State Intellectual Property Office of China on Dec. 24, 2019, entitled "METHOD AND DEVICE FOR CONTROLLING OUTPUT OF RADIOFREQUENCY ABLATION POWER, AND RADIOFREQUENCY ABLATION SYSTEM", the disclosure of which are incorporated herein by reference in their entities.

TECHNICAL FIELD

The present application relates to the field of medical technology, and more particularly, to a method and a device for controlling the output of radiofrequency ablation power, a radiofrequency ablation system, and a computer readable storage medium.

BACKGROUND

As an emerging technology in the medical field, radiofrequency ablation has been applied in the treatment of tumor diseases, neurological diseases and the like by now. The main mechanism of radiofrequency ablation is the thermal effect. When the radiofrequency current passes through the diseased tissue, the high frequency current causes the charged positive and negative ions in the diseased tissue to oscillate at high speed. The ions oscillating at high speed generate a large amount of heat by friction, thereby raising the temperature of the diseased tissue. Finally, the protein in the diseased cells is denatured, the intracellular water is lost, and the diseased tissue is coagulated and necrotic, so as to treat the diseased tissue by ablation.

During ablation, the impedance of the tissue changes along with the gradual drying of the tissue around the ablation electrode. If the temperature of the tissue around the ablation electrode is too high and rises too fast, the tissue near the ablation electrode will be charred, causing the impedance to increase sharply and phenomenon of "scab", causing the ablation to stop in advance, affecting the effective ablation range, performing the ablation halfway, and greatly affecting the ablation effect. In addition, if the ablation temperature is too high and the impedance changes sharply, the normal tissue around the ablation site will also be affected.

Therefore, how to avoid sharp changes in impedance, excessively high ablation temperature, ensure relatively uniform and continuous ablation, and avoid the phenomenon of "scab" at the same time are still technical challenges for those skilled in the art.

SUMMARY

In order to solve the above technical problems, the present application provides a method and a device for controlling the output of radiofrequency ablation power, a radiofrequency ablation system, and a computer readable storage medium.

A first aspect of the present application provides a method for controlling the output of radiofrequency ablation power. The method for controlling the output of radiofrequency ablation power includes:

setting an ablation parameter according to an input signal in an initial state, wherein the set ablation parameter comprises at least a preset ablation power;

issuing an ablation instruction to control a radiofrequency energy generator to output the preset ablation power upon receiving a start signal, recording an ablation time and acquiring an actual ablation parameter at an ablation site in real time, wherein the actual ablation parameter comprises at least an actual impedance;

determining whether the actual impedance meets a preset condition;

if the actual impedance meets the preset condition, issuing a sleep instruction to control the radiofrequency energy generator to pause the output of ablation power, recording a sleep time and pausing the recording of the ablation time; and if the sleep time exceeds a sleep time threshold, issuing the ablation instruction again to control the radiofrequency energy generator to continue the output of ablation power, and continuing the recording of the ablation time;

wherein the preset condition comprises a first preset condition and a second preset condition, the first preset condition is $R > K_1 * Rmin_1$, and the second preset condition is $R > K_2 * Rmin_2$, and wherein R is an actual impedance, $K_1$ and $K_2$ are proportionality coefficients and meet $K_1 < K_2$, $Rmin_1$ is the lowest impedance monitored in a preset period during recording the ablation time, and wherein the preset period is a period closest to a current time and having a preset time length, and $Rmin_2$ is the lowest impedance monitored during recording the ablation time;

determining whether the actual impedance meets the preset condition comprises determining whether the actual impedance meets any one of the first preset condition and the second preset condition; and if the actual impedance meets any one of the first preset condition and the second preset condition, determining that the actual impedance meets the preset condition.

A second aspect of the present application provides a device for controlling output of radiofrequency ablation power, comprising a memory and a processor, the memory having a computer program stored therein, wherein the processor, when executing the computer program, performs the steps of the method for controlling the output of radiofrequency ablation power according to the first aspect.

A third aspect of the present application provides a radiofrequency ablation system. The radiofrequency ablation system includes a radiofrequency energy generator, an ablation device, and the device for controlling the output of radiofrequency ablation power as described in the second aspect above. The radiofrequency energy generator is configured to provide radiofrequency energy required for radiofrequency ablation in a radiofrequency ablation procedure. The ablation device is electrically connected to the radiofrequency energy generator and is configured to be inserted into the ablation site during radiofrequency ablation, receive the radiofrequency energy output by the radiofrequency energy generator, and release the radiofrequency energy to the ablation site to perform radiofrequency ablation on the ablation site. The device for controlling the output of radiofrequency ablation power is electrically connected to the radiofrequency energy generator and is configured to control the radiofrequency energy generator to output the radiofrequency energy according to the set ablation parameter, the actual ablation parameter at the ablation site and an input from a user.

A fourth aspect of the present application provides a computer readable storage medium having a computer program stored therein. The computer program, when executed by a processor, performs the method for controlling the output of radiofrequency ablation power according to the first aspect.

The method and device for controlling the output of radiofrequency ablation power of the present application sets the first preset condition $R>K_1*Rmin_1$ and the second preset condition $R>K_2*Rmin_2$ at the same time, and the coefficients $K_1$ and $K_2$ meet $K_1<K_2$. If it is determined that the actual impedance meets any one of the first preset condition and the second preset condition, a sleep instruction will be issued to control the radiofrequency energy generator to pause the output of the ablation power. Not only the impedance change at the ablation site is kept in an intermittent stable state, an excessively high ablation temperature and the scab phenomenon can be avoided, and the radiofrequency energy can be output continuously, so that the radiofrequency ablation can be performed relatively uniformly in a circulating manner, thereby obtaining a satisfied therapeutic effect.

BRIEF DESCRIPTION OF THE DRAWINGS

In order to more clearly illustrate the technical solutions of the embodiments of the present application, the drawings accompanying the embodiments will be briefly described below, and it will be apparent that the drawings in the following description are some embodiments of the present application, for those skilled in the art, other drawings can be obtained from the drawings without creative labor.

Figure 1:
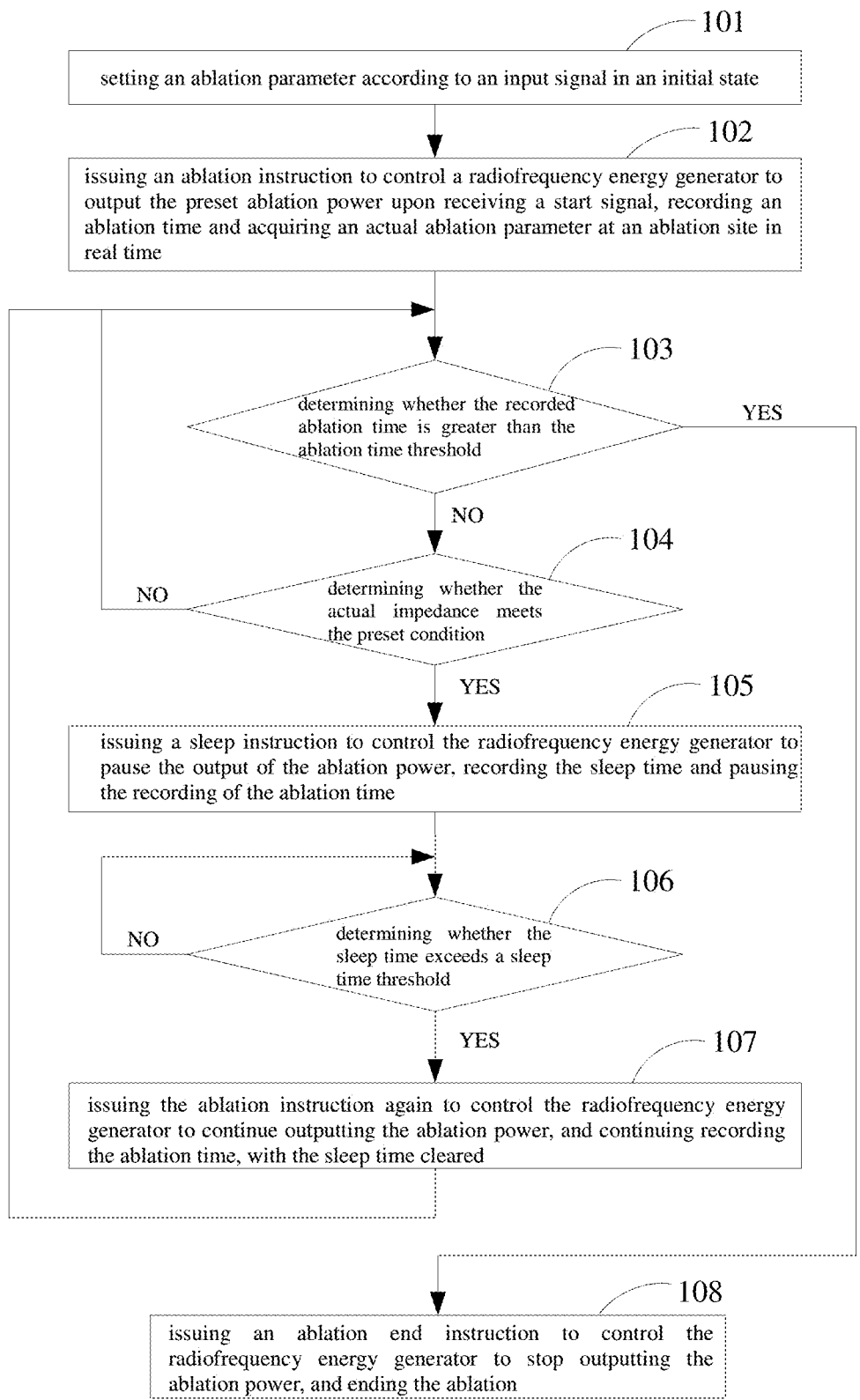
FIG. 1 is a flowchart of a method for controlling the output of radiofrequency ablation power according to an embodiment of the present application.

LIST OF REFERENCE NUMBERS FOR THE MAIN ELEMENTS radiofrequency ablation system 1000
device for controlling output of radiofrequency ablation power ("control device" in short) 600
processor 61
memory 62
computer program 621
input unit 63
display unit 64
alarm unit 65
radiofrequency energy generator 700
ablation device 800
ablation parameter detection device 900
steps 101~108, 11A, 12A~12B, 13A, 14A~14B, 15A~15B, 401~408, 501~507

The following detailed description will further explain the present application with reference to the above-mentioned drawings.

DESCRIPTION OF THE EMBODIMENTS

The technical solutions according to the embodiments of the present application will be clearly and fully described below with reference to the drawings accompanying the embodiments of the present application. The drawings are for illustrative purposes only, and are merely schematic drawings, and are not to be construed as limiting the present application. Apparently, the described embodiments are only part of, instead of all of the embodiments of the present application. All other embodiments obtained by the skilled person according to the embodiments disclosed in the present application without creative labor fall into the protection scope of the present application.

Unless otherwise defined, all technical and scientific terms used herein have the same meanings as commonly understood by those skilled in the art. The terminology used in the specification of this application is for the purpose of describing specific embodiments only and is not intended to limit this application.

FIG. 1 is a flowchart of a method for controlling the output of radiofrequency ablation power according to an embodiment of the present application. The method for controlling the output of radiofrequency ablation power can be applied to a device for controlling output of radiofrequency ablation power ("control device" in short), such as the control device 600 shown in FIG. 6 or FIG. 7. It should be noted that the method for controlling the output of radiofrequency ablation power described in the embodiments of the present application is not limited to the steps and sequences in the flowchart shown in FIG. 1. The steps in the illustrated flowchart can be added, removed, or the sequence therefor can be changed as required. As shown in FIG. 1, the method for controlling the output of radiofrequency ablation power includes the following steps.

Step 101: in an initial state, set an ablation parameter according to an input signal.

In this embodiment, the set ablation parameter at least includes parameters such as a preset ablation power, an ablation time threshold, a temperature threshold, an impedance threshold, and the like.

It will be appreciated that the control device can be provided with an input unit, such as mechanical key, mechanical knob, touch key, or touch panel that can display virtual key, and the input unit can receive input from a user, such as a healthcare worker, to generate corresponding input signal. For example, before the operation, the doctor can set parameters such as the preset ablation power, the ablation time threshold, the temperature threshold, and the impedance threshold according to factors such as the size of the area at the ablation site.

Step 102: when receiving a start signal, issue an ablation instruction to control a radiofrequency energy generator to output the preset ablation power, record the ablation time and obtain the actual ablation parameter at the ablation site in real time.

It will be appreciated that in the initial state, the output radiofrequency voltage of the radiofrequency energy generator is adjusted to the minimum, and the radiofrequency energy output is turned off.

In this embodiment, the actual ablation parameter includes at least actual impedance, actual ablation power, and actual ablation temperature.

The input unit can further include start key, pause key and stop key, wherein the start key generates a start signal upon receiving a pressing operation, the pause key generates a pause signal upon receiving a pressing operation, and the stop key generates a stop signal upon receiving a pressing operation. It will be appreciated that the start key and the pause key can be the same key so that the start signal and the pause signal are alternately generated upon receiving a pressing operation.

Figure 7:
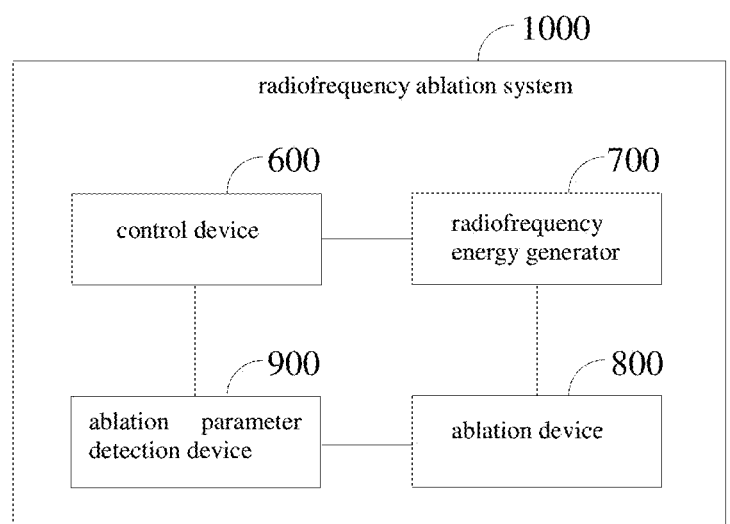
FIG. 7 is a schematic structural diagram of a radiofrequency ablation system provided by an embodiment of the present application.

In one embodiment, as shown in FIG. 7, the control device 600 can be electrically connected to a radiofrequency energy generator 700. The radiofrequency energy generator 700 is configured to generate a radiofrequency signal with a set power during the radiofrequency ablation to provide the radiofrequency energy required for the radiofrequency ablation. The control device 600 can control the radiofrequency energy generator 700 to output the radiofrequency energy according to the set ablation parameter, the actual ablation parameter at the ablation site, and the user's operation on the input unit.

The radiofrequency energy generator 700 can be further electrically connected to an ablation device 800, such as an ablation electrode. The ablation device 800 is inserted into the ablation site during radiofrequency ablation, receives the radiofrequency energy output by the radiofrequency energy generator 700, and releases the radiofrequency energy to the ablation site, so as to perform radiofrequency ablation on the ablation site, thereby treating the diseased tissue. The ablation site refers to a lesion site in a living body, such as a lesion tissue of a heart or other lesion tissue. Taking hypertrophic cardiomyopathy as an example, the ablation device 800 performs radiofrequency ablation on the hypertrophic myocardium of ventricular septum to treat hypertrophic cardiomyopathy by inserting the ablation device 800 into the heart of the patient via the apical access.

It will be appreciated that the radiofrequency energy generator 700 can be further electrically connected to a reference electrode plate. The reference electrode plate is attached at a suitable position on the patient's body during ablation. The electrode in the ablation device 800 and the reference electrode plate form a radiofrequency circuit via the human body. The high frequency current acts on the human tissue between the electrode in the ablation device 800 and the reference electrode plate, so that the tissue at the lesion site to which the electrode in the ablation device 800 is in contact is coagulated, denatured, and necrotized.

The control device 600 can be further electrically connected to an ablation parameter detection device 900 for monitoring the actual ablation parameter at the ablation site in real time.

In this embodiment, the ablation parameter detection device 900 can include an impedance detection module for detecting the actual impedance at the ablation site during ablation and transmitting the detected actual impedance to the control device 600. Specifically, the impedance detection module can be electrically connected with the radiofrequency circuit to acquire impedance of the radiofrequency circuit, thereby obtaining the actual impedance at the ablation site.

In this embodiment, the ablation parameter detection device 900 can further include a temperature detection module, such as a thermocouple or a thermistor. The temperature detection module can be provided on the ablation device 800 and inserted into the ablation site along with the ablation device 800 during ablation for detecting the actual ablation temperature at the ablation site and transmitting the detected actual ablation temperature to the control device 600.

In this embodiment, the ablation parameter detection device 900 can further include a voltage detection module and a current detection module. The voltage detection module can be connected in parallel with the radiofrequency circuit for detecting the ablation voltage in the radiofrequency circuit. The current detection module can be connected in series with the radiofrequency circuit for detecting the ablation current in the radiofrequency circuit. It will be appreciated that, in this embodiment, the actual ablation power can be calculated from the detected ablation voltage and ablation current.

Step 103: determine whether the recorded ablation time is greater than the ablation time threshold.

If the recorded ablation time is not greater than the ablation time threshold, step 104 is performed. Otherwise, if the recorded ablation time is greater than the ablation time threshold, step 108 is performed.

Step 104: determine whether the actual impedance meets the preset condition.

If the actual impedance meets the preset condition, step 105 is performed. Otherwise, if the actual impedance does not meet the preset condition, return to step 103, and continue monitoring whether the recorded ablation time is greater than the ablation time threshold.

In the present embodiment, the preset condition includes a first preset condition and a second preset condition, wherein the first preset condition is $R>K_1*Rmin_1$, and the second preset condition is $R>K_2*Rmin_2$, and wherein R is the actual impedance, $K_1$, $K_2$ are the proportionality coefficients, $Rmin_1$ is the lowest impedance monitored in a preset period during recording the ablation time, wherein the preset period is a period closest to the current time and having a preset time length, and $Rmin_2$ is the lowest impedance monitored during recording the ablation time.

In other words, the preset period is a period in the ablation period before the current time, with a preset time length $Rmin_2$ is the lowest impedance monitored during the ablation period from the ablation start time to the current time, or it can be understood as the lowest impedance during the whole ablation process from the start time to the current time.

In some embodiments, the preset time length can range from 15 s to 25 s.

For example, provided that the preset time length is 20 s and the timing is started from the time when the ablation is started, if the currently recorded ablation time is 10 s, $Rmin_1$ and $Rmin_2$ are both the lowest impedance monitored within 0 to 10 s, and if the currently recorded ablation time is 35 s, $Rmin_1$ is the lowest impedance monitored within 15-35 s, while $Rmin_2$ is the lowest impedance monitored within 0-35 s. It should be noted that the ablation period in the present embodiment does not include a period during which the radiofrequency energy generator pauses the output of the ablation power.

In this embodiment, the coefficients $K_1$ and $K_2$ meet $K_1<K_2$.

In some embodiments, $K_1$ ranges from 140% to 160%, and $K_2$ ranges from 180% to 220%.

In this embodiment, the step 104 specifically includes determining whether the actual impedance meets any one of a first preset condition and a second preset condition.

In the present embodiment, if the actual impedance meets any one of the first preset condition and the second preset condition, that is, if the actual impedance meets the first preset condition, or the actual impedance meets the first preset condition, or the actual impedance simultaneously meets the first preset condition and the second preset condition, the actual impedance meeting the preset condition can be determined.

Step 105: issue a sleep instruction to control the radiofrequency energy generator to pause the output of the ablation power, record the sleep time and pause the recording of the ablation time.

In this embodiment, the actual ablation parameter further includes the actual ablation power. The step 105 further includes recording the actual ablation power at the current time when the sleep instruction is issued.

Step 106: determine whether the sleep time exceeds a sleep time threshold.

If the sleep time exceeds the sleep time threshold, step 107 is performed. Otherwise, if the sleep time does not exceed the sleep time threshold, step 106 is continued to monitor whether the sleep time exceeds the sleep time threshold.

In the present application, the sleep time threshold is not specifically limited. It will be appreciated that the doctor can set a reasonable threshold in advance according to actual practice. For example, the sleep time threshold can be set to 15 s.

In step 107, issue the ablation instruction again to control the radiofrequency energy generator to continue outputting the ablation power, and continue recording the ablation time, with the sleep time cleared.

In the present embodiment, "issuing the ablation instruction again to control the radiofrequency energy generator to continue outputting the ablation power" in the step 107 specifically includes issuing the ablation instruction again to control the radiofrequency energy generator to continue outputting the actual ablation power recorded when the sleep instruction is issued.

After step 107, return to step 103 to continue monitoring whether the recorded ablation time is greater than the ablation time threshold.

Step 108: issue an ablation end instruction to control the radiofrequency energy generator to stop outputting the ablation power, and end the ablation.

In the present application, by setting the first preset condition $R>K_1*Rmin_1$, the impedance at the ablation site will change relatively stable during ablation.

Figure 2:
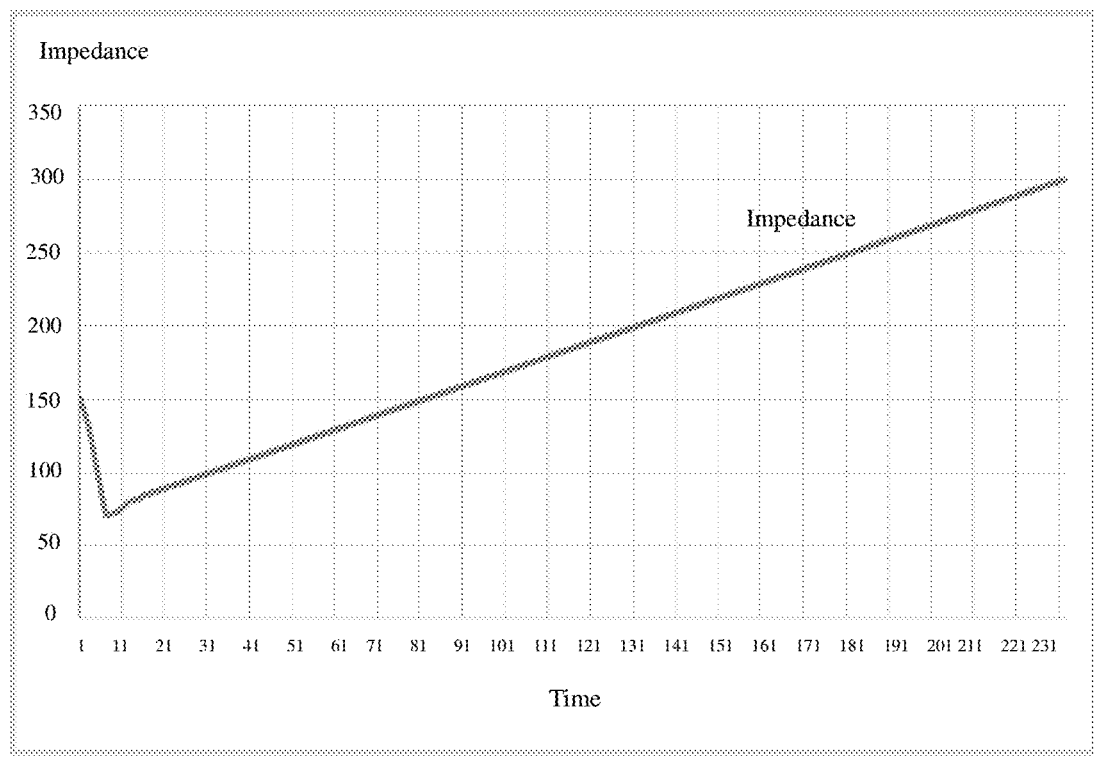
FIG. 2 is a schematic diagram of an impedance curve when only a first preset condition is set.

However, in the case where only the first preset condition is set, if the impedance at the ablation site rises slowly, as shown in FIG. 2, and the slope of the impedance curve is always smaller than the coefficient $K_1$, the actual impedance R will be always smaller than $K_1*Rmin_1$, that is, the actual impedance does not meet the first preset condition. Therefore, the actual impedance will continue rising slowly, the ablation will continue, and the ablation temperature will continue rising. When the actual impedance rises up to a certain level and the ablation temperature rises up to a certain level, "scab" phenomenon will occur at the ablation site, and even the normal tissue will be affected. In the case where an impedance threshold is preset to avoid the phenomenon "scab", the ablation will be stopped in advance when the actual impedance reaches the preset impedance threshold. These cases both lead to undesired ablation results and do not achieve the desired impedance control mode.

In the present application, by setting the second preset condition $R>K_2*Rmin_2$, the actual impedance would not rise too high during the whole ablation process, thereby avoiding the phenomenon "scab". In the treatment of hypertrophic cardiomyopathy by performing radiofrequency ablation on the hypertrophic myocardium of ventricular septum, once "scab" occurs, the diseased tissue at the scabbed site will be charred, which will hinder the heat conduction and thus affect the ablation on the diseased tissue around the "scab", resulting in incomplete ablation, and the charred tissue is difficult to be absorbed. Further, the "scab" will surround the distal end of the electrode in the ablation device 800 and hinder the withdrawal of the electrode. Therefore, "scab" should be particularly avoided when treating hypertrophic cardiomyopathy by radiofrequency ablation.

Figure 3:
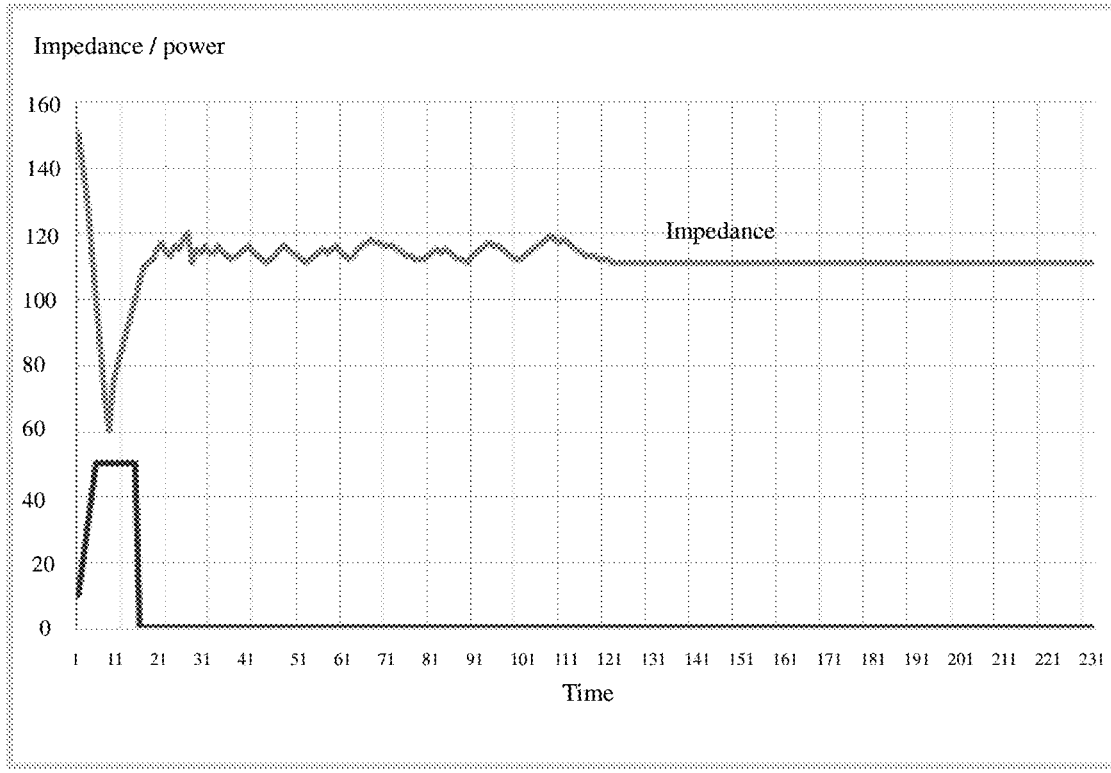
FIG. 3 is a schematic diagram of an impedance curve and a power curve when only a second preset condition is set.

However, in the case where only the second preset condition is set, if the coefficient $K_2$ is set too great, the impedance change cannot be kept in a stable state. If the coefficient $K_2$ is set too small, the impedance change is stable, however, as shown in FIG. 3, when the actual impedance is greater than $K_2*Rmin_2$, the radiofrequency energy generator will enter a sleep state and the output of the ablation power will be paused, and if the actual impedance keeps in a high state, the radiofrequency energy generator would not output ablation power, so that the ablation cannot be started again. The radiofrequency energy generator will sleep all the time without power output and the ablation will be terminated, resulting in incomplete ablation.

In the method for controlling the output of radiofrequency ablation power of the present application, both the first preset condition $R>K_1*Rmin_1$ and the second preset condition $R>K_2*Rmin_2$ are set, and the coefficients $K_1$ and $K_2$ meet $K_1<K_2$. If it is determined that the actual impedance meets any one of the first preset condition and the second preset condition, a sleep instruction will be issued to control the radiofrequency energy generator to pause the output of the ablation power. Not only the impedance change at the ablation site is kept in an intermittent stable state, an excessively high ablation temperature and the scab phenomenon can be avoided, and the radiofrequency energy can be output continuously, so that the radiofrequency ablation can be performed relatively uniformly in a circulating manner, thereby obtaining a satisfied therapeutic effect, especially for the treatment of hypertrophic cardiomyopathy.

In some embodiments, the method for controlling the output of radiofrequency ablation power further includes the following steps.

Step 11A: control the radiofrequency energy generator to output corresponding ablation power according to a power adjustment signal when the power adjustment signal is received.

It will be appreciated that the control device can further include a display unit for displaying the set ablation parameter, the recorded ablation time, the actual ablation parameter at the ablation site, the recorded sleep time, etc., to display the ablation status in real time, in such a way that the doctor can get the ablation condition by observing the data displayed on the display unit, and adjust the output of the radiofrequency power by operating the input unit.

In the operation, for example, the doctor can operate the input unit at any time according to data displayed on the display unit to cause the input unit to generate the corresponding power adjustment signal to adjust the ablation power output by the radiofrequency energy generator, keeping the temperature and impedance at the ablation site within the preset range, and thus the ablation device can perform radiofrequency ablation on the diseased tissue at the preset temperature based on the set ablation power.

In some embodiments, the method for controlling the output of radiofrequency ablation power further includes the following steps.

In step 12A, when a pause signal is received, issue an ablation pause instruction to control the radiofrequency energy generator to pause the output of the ablation power, and the recording of the ablation time is paused.

In step 12B, when a start signal is received again, issue the ablation instruction again to control the radiofrequency energy generator to continue outputting the ablation power, and the recording of the ablation time is continued.

It will be appreciated that, during the operation, the doctor can operate the input unit at any time according to the actual condition to cause the input unit to generate the pause signal and the start signal.

In this embodiment, the step 12A further includes:

Recording the actual ablation power at the current time when the ablation pause instruction is issued.

Accordingly, "issuing the ablation instruction again to control the radiofrequency energy generator to continue outputting the ablation power" in the step 12B specifically includes:

Issuing the ablation instruction again to control the radiofrequency energy generator to continue outputting the actual ablation power recorded when the ablation pause instruction is issued.

In some embodiments, the method for controlling the output of radiofrequency ablation power further includes the following steps.

In step 13A, when a stop signal is received, issue an ablation end instruction to control the radiofrequency energy generator 700 to stop outputting the ablation power, the ablation is ended.

It will be appreciated that, during the operation, the doctor can operate the input unit at any time according to the actual condition to cause the input unit to generate the stop signal. For example, when the predetermined ablation effect is achieved, the doctor can stop the ablation procedure in advance, i.e., turn off the output power of the radiofrequency energy generator, causing the ablation device to stop the ablation operation.

It will be appreciated that, as the "power adjustment signal" in step 11A, the "pause signal" in step 12A, the "start signal" in the step 12B and the "stop signal" in the step 13A are all signals triggered by human operation on the input unit, and therefore, the steps 11A, 12A, 12B, 13A can be performed at any time after the step 102 and before the step 108.

In some embodiments, the set ablation parameter further includes impedance threshold. The method for controlling the output of radiofrequency ablation power further includes the following steps.

In step 14A, determine whether the actual impedance exceeds the impedance threshold.

In step 14B, if the actual impedance exceeds the impedance threshold, issue an ablation stop instruction to control the radiofrequency energy generator to stop outputting ablation power.

In the present application, the impedance threshold is not specifically limited, and It will be appreciated that the doctor can set a reasonable threshold according to actual practice.

After step 14B, return to step 101, returning to the initial state.

It will be appreciated that the preset impedance threshold is generally set as a relatively high value within the safety threshold range, so as to avoid the "scab" phenomenon and ensure that the radiofrequency energy can be continuously output.

In some embodiments, the set ablation parameter further includes a temperature threshold, and the actual ablation parameter further includes the actual ablation temperature. The method for controlling the output of radiofrequency ablation power further includes the following steps.

In step 15A, determine whether the actual ablation temperature exceeds the temperature threshold.

In step 15B, if the actual ablation temperature exceeds the temperature threshold, issue an ablation stop instruction to control the radiofrequency energy generator to stop outputting ablation power.

In the present application, the temperature threshold is not specifically limited, and It will be appreciated that a doctor can set a reasonable threshold according to actual practice.

After step 15B, the flow returns to step 101, returning to the initial state.

It will be appreciated that the control device can further include an alarm unit. After the step 14B or the step 15B, the method for controlling the output of the radiofrequency ablation power can further include the step of issuing an alarm instruction to control the alarm unit to issue an alarm to indicate an abnormality.

The alarm unit can be an indicator lamp or a buzzer. The indicator lamp can indicate the abnormality by emitting light. Alternatively, the buzzer can indicate the abnormality by emitting a sound.

It will be appreciated that the actual impedance may exceed the impedance threshold at any time during ablation, and likewise, the actual ablation temperature may exceed the temperature threshold at any time, and therefore, the steps 14A, 14B, 15A, 15B can be performed at any time after the step 102 and before the step 108.

Figure 4:
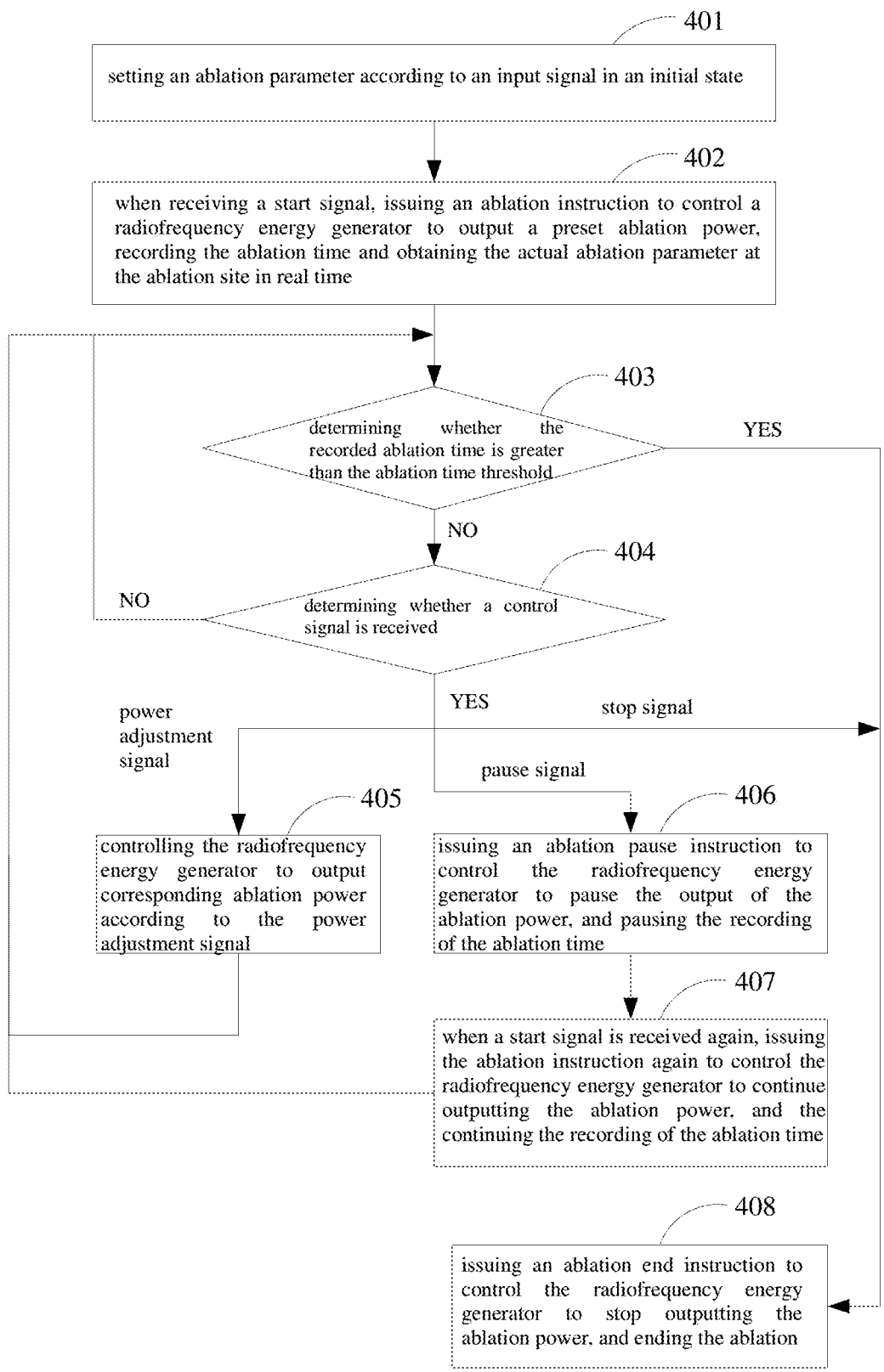
FIG. 4 is a flowchart of another method for controlling the output of radiofrequency ablation power according to an embodiment of the present application.

FIG. 4 is a flowchart of another method for controlling the output of radiofrequency ablation power according to an embodiment of the present application. The method for controlling the output of radiofrequency ablation power includes the following steps.

Step 401: in an initial state, set an ablation parameter according to an input signal.

Step 402: when receiving a start signal, issue an ablation instruction to control a radiofrequency energy generator to output a preset ablation power, record the ablation time and obtain the actual ablation parameter at the ablation site in real time.

Step 403: determine whether the recorded ablation time is greater than the ablation time threshold.

If the recorded ablation time is not greater than the ablation time threshold, step 404 is performed. Otherwise, if the recorded ablation time is greater than the ablation time threshold, step 408 is performed.

In step 404, determine whether a control signal is received. If the power adjustment signal is received, step 405 is performed; if the pause signal is receive, step 406 is performed; if the stop signal is received, step 408 is performed; if the control signal is not receive, return to step 403 and continue monitoring whether the recorded ablation time is greater than the ablation time threshold.

Step 405: control the radiofrequency energy generator to output corresponding ablation power according to the power adjustment signal.

After the step 405, return to step 403 and continue monitoring whether the recorded ablation time is greater than the ablation time threshold.

In step 406, issue an ablation pause instruction to control the radiofrequency energy generator to pause the output of the ablation power, and pause the recording of the ablation time.

Step 407: when a start signal is received again, issue the ablation instruction again to control the radiofrequency energy generator to continue outputting the ablation power, and the recording of the ablation time is continued.

After the step 407, return to step 403 and continue monitoring whether the recorded ablation time is greater than the ablation time threshold.

Step 408: issue an ablation end instruction to control the radiofrequency energy generator to stop outputting the ablation power, and end the ablation.

The details for the steps 401-408 according to the present embodiment can refer to the steps 101-103 and 108 according to the embodiment shown in FIG. 1 and the related details for the above steps 11A, 12A, 12B and 13A, which will not be repeated here.

In the present application, the input control signal is monitored during the ablation and corresponding control is performed according to the receive control signal, so that the doctor can conveniently control the ablation power output by the radiofrequency energy generator at any time according to the ablation condition during the operation, keeping the temperature and impedance at the ablation site within the preset range, and thus the ablation device can perform radiofrequency ablation on the diseased tissue at the preset temperature based on the set ablation power, thereby effectively avoiding the phenomenon of "scab".

Figure 5:
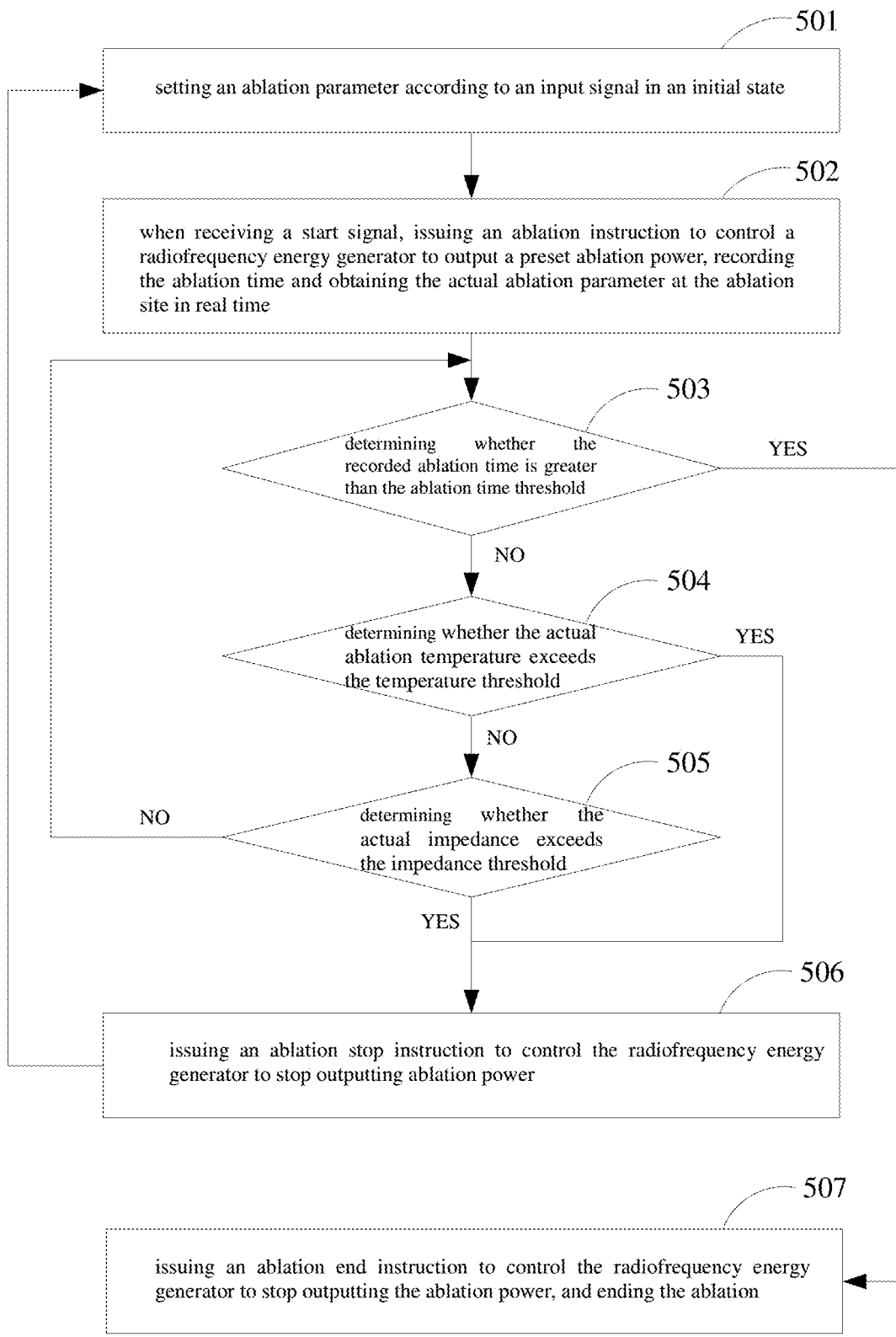
FIG. 5 is a flowchart of a further method for controlling the output of radiofrequency ablation power according to an embodiment of the present application.

FIG. 5 is a flowchart of a further method for controlling the output of radiofrequency ablation power according to an embodiment of the present application. The method for controlling the output of radiofrequency ablation power includes the following steps.

Step 501: in an initial state, set an ablation parameter according to an input signal.

Step 502: when receiving a start signal, issue an ablation instruction to control a radiofrequency energy generator to output a preset ablation power, record the ablation time and obtain the actual ablation parameter at the ablation site in real time.

Step 503: determine whether the recorded ablation time is greater than the ablation time threshold.

If the recorded ablation time is not greater than the ablation time threshold, step 504 is performed. Otherwise, if the recorded ablation time is greater than the ablation time threshold, step 507 is performed.

Step 504: determine whether the actual ablation temperature exceeds the temperature threshold.

If the actual ablation temperature does not exceed the temperature threshold, step 505 is performed. Otherwise, if the actual ablation temperature exceeds the temperature threshold, step 506 is performed.

Step 505: determine whether the actual impedance exceeds the impedance threshold.

If the actual impedance exceeds the impedance threshold, step 506 is performed. Otherwise, if the actual impedance does not exceed the impedance threshold, return to step 503, and continue monitoring whether the recorded ablation time is greater than the ablation time threshold.

It will be appreciated that the sequence of the step 504 and the step 505 can be changed.

In step 506, issue an ablation stop instruction to control the radiofrequency energy generator to stop outputting ablation power, and return to step 501.

Step 507: issue an ablation end instruction to control the radiofrequency energy generator to stop outputting the ablation power, and end the ablation.

The details for the steps 501-507 of the present embodiment can refer to the steps 101-103 and 108 according to the embodiment shown in FIG. 1 and the related details for the above steps 14A, 14B, 15A and 15B, which will not be repeated here.

By monitoring the actual ablation temperature and the actual impedance during ablation, and controlling the radiofrequency energy generator to stop outputting the ablation power in time when the actual ablation temperature exceeds the temperature threshold or the actual impedance exceeds the impedance threshold, the phenomenon of "scab" can be effectively avoided.

Figure 6:
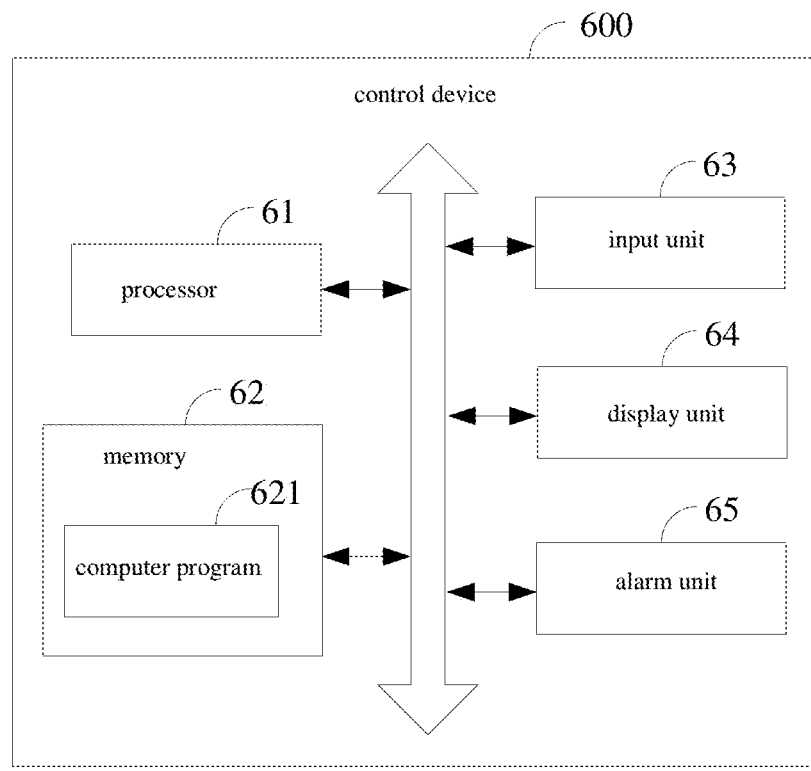
FIG. 6 is a schematic structural diagram of a device for controlling the output of radiofrequency ablation power provided by an embodiment of the present application.

FIG. 6 is a schematic structural diagram of a device 600 for controlling the output of radiofrequency ablation power according to an embodiment of the present application (in short, control device). The control device 600 can be used in a radiofrequency ablation system.

FIG. 7 is a schematic structural diagram of a radiofrequency ablation system 1000 according to an embodiment of the present application. The radiofrequency ablation system 1000 includes a control device 600, a radiofrequency energy generator 700, an ablation device 800, and an ablation parameter detection device 900.

The control device 600 is electrically connected to the radiofrequency energy generator 700. The radiofrequency energy generator 700 is used for generating radiofrequency signal with a set power during radiofrequency ablation, to provide the radiofrequency energy required for radiofrequency ablation. The control device 600 can control the radiofrequency energy generator 700 to output the radiofrequency energy according to the set ablation parameter, the actual ablation parameter at the ablation site, and the input from the user.

In this embodiment, the control device 600 and the radiofrequency energy generator 700 can be two independent devices. Alternatively, the control device 600 and the radiofrequency energy generator 700 can be provided in the same device. That is, this device functions as a radiofrequency energy generator and a control device for the output of radiofrequency ablation power.

The radiofrequency energy generator 700 is further electrically connected to the ablation device 800, such as an ablation electrode, which is inserted into the ablation site during radiofrequency ablation, receives the radiofrequency energy output by the radiofrequency energy generator 700, and releases the radiofrequency energy to the ablation site, so as to perform radiofrequency ablation on the ablation site, thereby treating the diseased tissue. The ablation site refers to a lesion site in a living body, such as a lesion tissue of a heart or other lesion tissue.

In the present embodiment, the radiofrequency energy generator 700 is further electrically connected to a reference electrode plate (not shown) which is attached at a suitable position on the patient's body during ablation. The electrode in the ablation device 800 and the reference electrode plate form a radiofrequency circuit via the human body. The high frequency current acts on the human tissue between the electrode in the ablation device 800 and the reference electrode plate, so that the tissue at the lesion site to which the electrode in the ablation device 800 is in contact is coagulated, denatured, and necrotized.

The control device 600 is further electrically connected to the ablation parameter detection device 900 for monitoring the actual ablation parameter at the ablation site in real time.

In this embodiment, the ablation parameter detection device 900 can include an impedance detection module, a temperature detection module, a voltage detection module, a current detection module, and the like.

The impedance detection module is configured for detecting the actual impedance at the ablation site during ablation and transmitting the detected actual impedance to the control device 600. Specifically, the impedance detection module can be electrically connected with the radiofrequency circuit to acquire impedance of the radiofrequency circuit, thereby obtaining the actual impedance at the ablation site.

The temperature detection module can be a thermocouple, a thermistor, or the like. The temperature detection module can be provided on the ablation device 800 and inserted into the ablation site along with the ablation device 800 during ablation for detecting the actual ablation temperature at the ablation site and transmitting the detected actual ablation temperature to the control device 600.

The voltage detection module can be connected in parallel with the radiofrequency circuit for detecting the ablation voltage in the radiofrequency circuit. The current detection module can be connected in series with the radiofrequency circuit for detecting the ablation current in the radiofrequency circuit. It will be appreciated that, in this embodiment, the actual ablation power can be calculated from the detected ablation voltage and ablation current.

Referring to FIG. 6, the control device 600 includes at least a processor 61, a memory 62, an input unit 63, and a display unit 64. Those skilled in the art can understand that the schematic diagram FIG. 6 only shows an example of the control device 600 for implementing the method for controlling output of the radiofrequency ablation power, and should not be construed as limiting the control device 600. More or fewer components than the illustrated can be included. Alternatively, some components can be combined. Alternatively, different components can be included. For example, the control device 600 can further include a network access device or the like.

The input unit 63 can include, for example, but is not limited to, mechanical key, mechanical knob, touch key, or touch panel that can display virtual key, and can receive input from a user, such as a healthcare worker, to generate corresponding input signal. For example, before the operation, the doctor can set parameters such as the preset ablation power, the ablation time threshold, the temperature threshold, and the impedance threshold according to factors such as the size of the area at the ablation site.

The input unit 63 can further include start key, pause key and stop key, wherein the start key generates a start signal upon receiving a pressing operation, the pause key generates a pause signal upon receiving a pressing operation, and the stop key generates a stop signal upon receiving a pressing operation. It will be appreciated that the start key and the pause key can be the same key so that the start signal and the pause signal are alternately generated upon receiving a pressing operation.

For example, before the operation, the doctor can start the ablation by pressing the start key. During the operation, the doctor can operate the input unit 63 at any time according to the ablation condition to control the ablation power output by the radiofrequency energy generator 700, keeping the temperature and impedance at the ablation site within the preset range, and thus the ablation device 800 can perform radiofrequency ablation on the diseased tissue at the preset temperature based on the set ablation power, thereby effectively avoiding the "scab" phenomenon.

The memory 62 can include high-speed random access memory, and can further include non-volatile memory such as hard disk, memory, plug-in hard disk, smart memory card (SMC), secure digital (SD), flash card, at least one disk memory device, flash memory device, or other volatile solid state memory device.

A computer program 621 is stored in the memory 62. The computer program 621 can be divided into one or more modules/units which are stored in the memory 62 and executed by the processor 61 to perform the method for controlling the output of the radiofrequency ablation power of the present application. The one or more modules/units can be a series of computer program instruction segments capable of performing particular function and used to describe the execution of the computer program 621 in the control device 600.

The processor 61 can be a central processing unit (CPU), or other general purpose processor, digital signal processor (DSP), application specific integrated circuits (ASIC), Field-Programmable Gate Array (FPGA), or other programmable logic device, discrete gate or transistor logic device, discrete hardware component, etc. The general purpose processor can be a microprocessor. Alternatively, the processor can be any conventional processor or the like. The processor 61 is the control center of the control device 600, and connected to the components of the control device 600 via interfaces and lines. The processor 61 implements various functions of the control device 600 by running or executing the computer program 621 and/or modules/units stored in the memory 62 and loading data stored in the memory 62.

In this embodiment, the processor 61 executes the computer program 621 to perform the steps in the embodiments of the method for controlling the output of radiofrequency ablation power, such as steps 101 to 108 shown in FIG. 1, steps 401 to 408 shown in FIG. 4, or steps 501 to 507 shown in FIG. 5.

Specifically, the processor 61 is configured to run the computer program 621 stored in the memory 62 to perform the following steps:

Setting an ablation parameter according to an input signal in an initial state, wherein the set ablation parameter includes at least a preset ablation power;

Issuing an ablation instruction to control the radiofrequency energy generator to output the preset ablation power upon receiving the start signal, and recording the ablation time and obtaining the actual ablation parameter at the ablation site in real time, wherein the actual ablation parameter includes at least an actual impedance;

Determining whether the actual impedance meets a preset condition;

If the actual impedance meets the preset condition, a sleep instruction is issued to control the radiofrequency energy generator to pause the output of ablation power, and the sleep time is recorded and the recording of the ablation time is paused;

If the sleep time exceeds the sleep time threshold, the ablation instruction is issued again to control the radiofrequency energy generator to continue outputting the ablation power, and continue recording the ablation time.

In the present embodiment, the preset condition includes a first preset condition and a second preset condition, wherein the first preset condition is $R > K_1 * Rmin_1$, and the second preset condition is $R > K_2 * Rmin_2$, and wherein R is the actual impedance, $K_1$, $K_2$ are the proportionality coefficients, $Rmin_1$ is the lowest impedance monitored in a preset period during recording the ablation time, wherein the preset period is a period closest to the current time and having a preset time length, and $Rmin_2$ is the lowest impedance monitored during recording the ablation time.

In some embodiments, the preset time length can range from 15 s to 25 s.

In this embodiment, the coefficients $K_1$ and $K_2$ meet $K_1 < K_2$.

In some embodiments, $K_1$ ranges from 140% to 160%, and $K_2$ ranges from 180% to 220%.

In this embodiment, the processor 61 is specifically configured to perform the following steps when executing the step of "determining whether the actual impedance meets the preset condition":

Determining whether the actual impedance meets any one of a first preset condition and a second preset condition.

In the present embodiment, if the actual impedance meets any one of the first preset condition and the second preset condition, that is, if the actual impedance meets the first preset condition, or the actual impedance meets the first preset condition, or the actual impedance simultaneously meets the first preset condition and the second preset condition, the actual impedance meeting the preset condition can be determined.

In the device for controlling the output of radiofrequency ablation power of the present application, both the first preset condition $R > K_1 * Rmin_1$ and the second preset condition $R > K_2 * Rmin_2$ are set, and the coefficients $K_1$ and $K_2$ meet $K_1 < K_2$. If it is determined that the actual impedance meets any one of the first preset condition and the second preset condition, a sleep instruction will be issued to control the radiofrequency energy generator to pause the output of the ablation power. Not only the impedance change at the ablation site is kept in an intermittent stable state, an excessively high ablation temperature and the scab phenomenon can be avoided, and the radiofrequency energy can be output continuously, so that the radiofrequency ablation can be performed relatively uniformly in a circulating manner, thereby obtaining a satisfied therapeutic effect.

In some embodiments, the actual ablation parameter further includes the actual ablation power.

The processor 61 is further configured to run the computer program 621 stored in the memory 62 to perform the following steps:

Recording the actual ablation power at the current time when the sleep instruction is issued.

In this embodiment, the processor 61 is specifically configured to perform the following steps when executing "issuing the ablation instruction again to control the radiofrequency energy generator to continue outputting the ablation power":

Issuing the ablation instruction again to control the radiofrequency energy generator to continue outputting the actual ablation power recorded when the sleep instruction is issued.

In some embodiments, the processor 61 is further configured to run the computer program 621 stored in the memory 62 to perform the following steps:

Controlling the radiofrequency energy generator to output corresponding ablation power according to a power adjustment signal when the power adjustment signal is received.

The display unit 64 can be configured for displaying the set ablation parameter, the recorded ablation time, the actual ablation parameter at the ablation site, the recorded sleep time, etc., to display the ablation status in real time, in such a way that the doctor can get the ablation condition by observing the data displayed on the display unit 64, and adjust the output of the radiofrequency power by operating the input unit 63.

In some embodiments, the set ablation parameter further includes an ablation time threshold.

The processor 61 is further configured to run the computer program 621 stored in the memory 62 to perform the following steps:

Determining whether the recorded ablation time is greater than the ablation time threshold;

If the recorded ablation time is greater than the ablation time threshold, issue an ablation end instruction to control the radiofrequency energy generator to stop outputting ablation power.

In some embodiments, the processor 61 is further configured to run the computer program 621 stored in the memory 62 to perform the following steps:

Upon receiving a pause signal, issuing an ablation pause instruction to control the radiofrequency energy generator to pause the output of the ablation power, and pausing the recording of the ablation time;

Upon receiving the start signal again, issuing the ablation instruction again to control the radiofrequency energy generator to continue outputting the ablation power, and continuing the recording of the ablation time.

In this embodiment, the actual ablation parameter further includes the actual ablation power. The processor 61 is further configured to run the computer program 621 stored in the memory 62 to perform the following steps:

Recording the actual ablation power at the current time when the ablation pause instruction is issued.

In this embodiment, the processor 61 is specifically configured to perform the following steps when executing the step of "upon receiving the start signal again, issuing the ablation instruction again to control the radiofrequency energy generator to continue outputting the ablation power":

Upon receiving the start signal again, issuing the ablation instruction again to control the radiofrequency energy generator to continue outputting the actual ablation power recorded when the ablation pause instruction is issued.

In some embodiments, the processor 61 is further configured to run the computer program 621 stored in the memory 62 to perform the following steps:

Upon receiving a stop signal, issuing an ablation end instruction to control the radiofrequency energy generator to stop outputting the ablation power.

In some embodiments, the set ablation parameter further includes an impedance threshold.

The processor 61 is further configured to run the computer program 621 stored in the memory 62 to perform the following steps:

Determining whether the actual impedance exceeds the impedance threshold;

If the actual impedance exceeds the impedance threshold, issue an ablation stop instruction to control the radiofrequency energy generator to stop outputting ablation power.

In some embodiments, the set ablation parameter further includes a temperature threshold, and the actual ablation parameter further includes an actual ablation temperature.

The processor 61 is further configured to run the computer program 621 stored in the memory 62 to perform the following steps:

Determining whether the actual ablation temperature exceeds the temperature threshold;

If the actual ablation temperature exceeds the temperature threshold, issue an ablation stop instruction to control the radiofrequency energy generator to stop outputting ablation power.

The specific technical details of the present embodiment can refer to the related technical details of the above embodiments of the method for controlling the output of the radiofrequency ablation power, which would not be repeated herein.

The embodiments of the present application further provide a computer readable storage medium having a computer program stored therein. The computer program, when executed by the processor, implements the steps in the above embodiments of the method for controlling the output of the radiofrequency ablation power, such as steps 101 to 108 shown in FIG. 1, steps 401 to 408 shown in FIG. 4, or steps 501-507 shown in FIG. 5. The specific technical details of the present embodiment can refer to the related technical details of the above embodiments of the method for controlling the output of the radiofrequency ablation power, which would not be repeated herein.

If the integrated module/unit of the radiofrequency ablation power output control device/computer device of the present application is implemented in the form of a software functional unit and sold or used as a separate product, it can be stored in a computer readable storage medium. Based on this, all or part of the flow in the embodiments of the method for controlling the output of the radiofrequency ablation power described above can be implemented by instructing relevant hardware through the computer program. The computer program can be stored in a computer readable storage medium, and the computer program, when executed by the processor, can implement the steps of the above embodiments of the method for controlling the output of the radiofrequency ablation power. The computer program includes computer program code, which can be in the form of source code, object code, executable file or some intermediate form, etc. The computer readable medium can include any entity or device capable of carrying the computer program code, a recording medium, a U-disk, a mobile hard disk, a magnetic disk, an optical disk, a computer memory, a read only memory (ROM), random access memory (RAM), electrical carrier signals, telecommunications signals, software distribution media, and the like. It should be noted that the contents contained in the computer readable medium can be appropriately varied according to the requirements of the legislation in the jurisdiction and patent practice. For example, in some jurisdictions, according to the legislation and patent practice, the computer readable medium does not include electrical carrier signals and telecommunications signals.

It will be apparent to those skilled in the art that the present application is not limited to the details of the exemplary embodiments described above, and that the present application can be embodied in other specific forms without departing from the spirit or essential characteristics of the present application. Thus, the embodiments are exemplary and are not to be construed as limiting the present application. The scope of the present application is defined by the appended claims rather than the foregoing description. It is therefore intended that all changes falling within the meaning and scope of the equivalent elements of the claims be encompassed by this application. Any reference signs in the claims should not be taken as limiting the claims to which they relate. Moreover, it is clear that the word "comprising" does not exclude other elements or steps and that the singular does not exclude the plural.

Finally, it should be noted that the above embodiments are merely intended to illustrate the technical solutions of the present application and are not limited thereto, and although the present application has been described in detail with reference to the above preferred embodiments, it should be understood by those of ordinary skill in the art, modifications or equivalent substitutions that can be made to the technical solutions of the present application should not depart from the spirit and scope of the technical solutions of the present application.

What is claimed is:

1. A method for controlling output of radiofrequency ablation power, comprising steps of:
setting an ablation parameter according to an input signal in an initial state, wherein the set ablation parameter comprises at least a preset ablation power;
issuing an ablation instruction to control a radiofrequency energy generator to output the preset ablation power upon receiving a start signal, recording an ablation time and acquiring an actual ablation parameter at an ablation site in real time, wherein the actual ablation parameter comprises at least an actual impedance;
determining whether the actual impedance meets a preset condition;
if the actual impedance meets the preset condition, issuing a sleep instruction to control the radiofrequency energy generator to pause the output of ablation power, recording a sleep time and pausing the recording of the ablation time; and
if the sleep time exceeds a sleep time threshold, issuing the ablation instruction again to control the radiofrequency energy generator to continue the output of ablation power, and continuing the recording of the ablation time;
wherein the preset condition comprises a first preset condition and a second preset condition, the first preset condition is $R > K_1 * Rmin_1$, and the second preset condition is $R > K_2 * Rmin_2$, and wherein R is an actual impedance, $K_1$ and $K_2$ are proportionality coefficients and meet $K_1 < K_2$, $Rmin_1$ is the lowest impedance monitored in a preset period during recording the ablation time, and wherein the preset period is a period closest to a current time and having a preset time length, and $Rmin_2$ is the lowest impedance monitored during recording the ablation time;
determining whether the actual impedance meets the preset condition comprises determining whether the actual impedance meets any one of the first preset condition and the second preset condition; and
if the actual impedance meets any one of the first preset condition and the second preset condition, determining that the actual impedance meets the preset condition.

2. The method for controlling the output of radiofrequency ablation power according to claim 1, wherein the $K_1$ ranges from 140% to 160%, and the $K_2$ ranges from 180% to 220%.

3. The method for controlling the output of radiofrequency ablation power according to claim 1, wherein the preset time length ranges from 15 s to 25 s.

4. The method for controlling the output of radiofrequency ablation power according to claim 1, further comprising:
controlling the radiofrequency energy generator to output corresponding ablation power according to a power adjustment signal upon receiving the power adjustment signal.

5. The method for controlling the output of radiofrequency ablation power according to claim 4, wherein the actual ablation parameter further comprises an actual ablation power, and the method for controlling the output of radiofrequency ablation power further comprises:
recording the actual ablation power at the current time upon issuing the sleep instruction; and
said "issuing the ablation instruction again to control the radiofrequency energy generator to continue the output of ablation power" comprises:
issuing the ablation instruction again to control the radiofrequency energy generator to continue the output of the recorded actual ablation power.

6. The method for controlling the output of radiofrequency ablation power according to claim 1, wherein the set ablation parameter further comprises an ablation time threshold, and the method for controlling the output of radiofrequency ablation power further comprises:
determining whether the recorded ablation time is greater than the ablation time threshold; and
if the recorded ablation time is greater than the ablation time threshold, issuing an ablation end instruction to control the radiofrequency energy generator to stop the output of ablation power.

7. The method for controlling the output of radiofrequency ablation power according to claim 6, further comprising:
upon receiving a pause signal, issuing an ablation pause instruction to control the radiofrequency energy generator to pause the output of ablation power, and pausing the recording of the ablation time.

8. The method for controlling the output of radiofrequency ablation power according to claim 7, further comprising:
upon receiving the start signal again, issuing the ablation instruction again to control the radiofrequency energy generator to continue the output of ablation power, and continuing the recording of the ablation time.

9. The method for controlling the output of radiofrequency ablation power according to claim 8, wherein the actual ablation parameter further comprises an actual ablation power, and the method for controlling the output of radiofrequency ablation power further comprises:
recording the actual ablation power at the current time upon issuing the ablation pause instruction; and
said "upon receiving the start signal again, issuing the ablation instruction again to control the radiofrequency energy generator to continue the output of ablation power" comprises:
upon receiving the start signal again, issuing the ablation instruction again to control the radiofrequency energy generator to continue the output of the recorded actual ablation power.

10. The method for controlling the output of radiofrequency ablation power according to claim 6, further comprising:
upon receiving a stop signal, issuing the ablation end instruction to control the radiofrequency energy generator to stop the output of ablation power.

11. The method for controlling the output of radiofrequency ablation power according to claim 6, wherein the set ablation parameter further comprises an impedance threshold, and the method for controlling the output of radiofrequency ablation power further comprises:
determining whether the actual impedance exceeds the impedance threshold; and
if the actual impedance exceeds the impedance threshold, issuing an ablation stop instruction to control the radiofrequency energy generator to stop the output of ablation power.

12. The method for controlling the output of radiofrequency ablation power according to claim 6, wherein the set ablation parameter further comprises a temperature threshold, and the actual ablation parameter further comprises an actual ablation temperature, and the method for controlling the output of radiofrequency ablation power further comprises:
determining whether the actual ablation temperature exceeds the temperature threshold; and
if the actual ablation temperature exceeds the temperature threshold, issuing an ablation stop instruction to control the radiofrequency energy generator to stop the output of ablation power.

13. A device for controlling output of radiofrequency ablation power, comprising a memory and a processor, the memory having a computer program stored therein, wherein the processor, when executing the computer program, performs the steps of the method for controlling the output of radiofrequency ablation power according to claim 1.

14. The device for controlling the output of radiofrequency ablation power according to claim 13, wherein the K1 ranges from 140% to 160%, and the K2 ranges from 180% to 220%.

15. The device for controlling the output of radiofrequency ablation power according to claim 13, wherein the actual ablation parameter further comprises an actual ablation power, and the method for controlling the output of radiofrequency ablation power further comprises:
recording the actual ablation power at the current time upon issuing the sleep instruction; and
said "issuing the ablation instruction again to control the radiofrequency energy generator to continue the output of ablation power" comprises:
issuing the ablation instruction again to control the radiofrequency energy generator to continue the output of the recorded actual ablation power.

16. A radiofrequency ablation system, comprising a radiofrequency energy generator, an ablation device, and the device for controlling the output of radiofrequency ablation power according to claim 13, wherein,
the radiofrequency energy generator is configured to provide radiofrequency energy required for radiofrequency ablation in a radiofrequency ablation procedure;
the ablation device is electrically connected to the radiofrequency energy generator and is configured to be inserted into the ablation site during radiofrequency ablation, receive the radiofrequency energy output by the radiofrequency energy generator, and release the radiofrequency energy to the ablation site to perform radiofrequency ablation on the ablation site, and
the device for controlling the output of radiofrequency ablation power is electrically connected to the radiofrequency energy generator and is configured to control the radiofrequency energy generator to output the radiofrequency energy according to the set ablation parameter, the actual ablation parameter at the ablation site and an input from a user.

17. The radiofrequency ablation system according to claim 16, wherein the K1 ranges from 140% to 160%, and the K2 ranges from 180% to 220%.

18. The radiofrequency ablation system according to claim 16, wherein the actual ablation parameter further comprises an actual ablation power, and the method for controlling the output of radiofrequency ablation power further comprises:
- recording the actual ablation power at the current time upon issuing the sleep instruction; and
- said "issuing the ablation instruction again to control the radiofrequency energy generator to continue the output of ablation power" comprises:
- issuing the ablation instruction again to control the radiofrequency energy generator to continue the output of the recorded actual ablation power.

19. A computer readable storage medium, having a computer program stored therein, wherein the computer program, when executed by a processor, performs the method for controlling the output of radiofrequency ablation power according to claim 1.

20. The computer readable storage medium according to claim 19, wherein the actual ablation parameter further comprises an actual ablation power, and the method for controlling the output of radiofrequency ablation power further comprises:
- recording the actual ablation power at the current time upon issuing the sleep instruction; and
- said "issuing the ablation instruction again to control the radiofrequency energy generator to continue the output of ablation power" comprises:
- issuing the ablation instruction again to control the radiofrequency energy generator to continue the output of the recorded actual ablation power.

* * * * *